(12) United States Patent
Choi et al.

(10) Patent No.: US 6,884,440 B2
(45) Date of Patent: Apr. 26, 2005

(54) COMPOSITION OF MULTIPURPOSE HIGH FUNCTIONAL ALKALINE SOLUTION COMPOSITION, PREPARATION THEREOF, AND FOR THE USE OF NONSPECIFIC IMMUNOSTIMULATOR

(75) Inventors: Soo-Il Choi, Ansung (KR); Hyun-Suk Choi, Ansung (KR); Kyung-Soo Jeon, Ansung (KR); Byung-Woo Yoo, Seoul (KR); Yong-Ho Park, Seoul (KR)

(73) Assignee: Barodon-S.F. Corp., Kyunggi-Do (KR)

( * ) Notice: Subject to any disclaimer, the term of this patent is extended or adjusted under 35 U.S.C. 154(b) by 0 days.

(21) Appl. No.: 10/422,696

(22) Filed: Apr. 25, 2003

(65) Prior Publication Data

US 2003/0206967 A1 Nov. 6, 2003

Related U.S. Application Data

(62) Division of application No. 10/043,162, filed on Jan. 14, 2002, now Pat. No. 6,673,375, which is a division of application No. 09/755,020, filed on Jan. 8, 2001, now Pat. No. 6,447,810.

(30) Foreign Application Priority Data

Nov. 23, 2000 (KR) ......................................... 2000-70054

(51) Int. Cl.⁷ ...................... A61K 33/00; A61K 33/04; A61K 33/22; A61K 31/7016; A61K 35/08
(52) U.S. Cl. ...................... 424/658; 424/711; 424/715; 424/722; 514/53; 514/874; 514/885
(58) Field of Search ................................ 424/658, 711, 424/715, 722; 514/53, 874, 885

(56) References Cited

PUBLICATIONS

Chemical Abstracts 133: 181581, abstracting KR 128110 (Apr. 1998).*
Chemical Abstracts 133:181581, abstracting KR 128110 (Apr. 1998).*

* cited by examiner

*Primary Examiner*—John Pak
(74) *Attorney, Agent, or Firm*—Piper Rudnick LLP

(57) ABSTRACT

Disclosed are a multipurpose, high-functional, alkaline solution composition, preparation therefor and use thereof as a nonspecific immunostimulator. The composition comprises 1–25 parts by weight of borax ($Na_2B_4O_7 \cdot 10H_2O$), $10^{-5}$–$10^{-4}$ parts by weight of sodium thiosulfate ($Na_2S_2O_3 \cdot 5H_2O$), 30–150 parts by weight of potassium carbonate, 30–200 parts by weight of refined sugar ($C_{12}H_{22}O_{11}$), and 100–200 parts by weight of water, based on 100 parts by weight of sodium metasilicate ($Na_2SiO_3 \cdot 5H_2O$). In addition to bringing about an improvement in disease resistance, weight gain rate, crop yield, crop quality, harvest time, the composition shows nonspecific immunostimulating activities, including antibody production and immune enhancement, by activating immune cells, thereby maximizing vaccination effects on malignant viral diseases.

1 Claim, 11 Drawing Sheets

COMPOSITION OF MULTIPURPOSE HIGH FUNCTIONAL ALKALINE SOLUTION COMPOSITION, PREPARATION THEREOF, AND FOR THE USE OF NONSPECIFIC IMMUNOSTIMULATOR

This is a divisional application of prior Ser. No. 10/043,162 filed Jan. 14, 2002 which is now U.S. Pat. No. 6,673,375, which is a divisional application of application Ser. No. 09/755,020 filed Jan. 8, 2001, which is now U.S. Pat. No. 6,447,810.

BACKGROUND OF THE INVENTION

Field of the invention

The present invention relates to a multi-purpose, high-functional, alkaline solution composition, a preparation method therefor, and use thereof as an nonspecific immunostimulator. More particularly, the present invention relates to an alkaline solution composition which mostly comprises sodium metasilicate (pentahydrate) and shows nonspecific immunostimulating activities, including antibody production and immune enhancement, by activating immune cells, thereby maximizing vaccination effects versus malignant virus diseases, preparation therefor, and use thereof as an immunostimulator. 2. Description of the Prior Art The functionality of alkaline mass in the body has been of great interest since the early $20^{th}$ century. Extensive research has recently revealed that alkaline mass in the body increases ionization ratios of potassium and sodium to heighten the purification capability of blood, resulting in blood clearance, fatigue-reduction, and aging retardation.

One alkaline solution composition is disclosed in Korean Pat. No. 128,110, yielded to the present inventor, which comprises 10–18 parts by weight of sodium silicate, 0.1–0.5 parts by weight of sodium hyperoxide, 5–10 parts by weight of potassium carbonate, 1 part by weight of sodium carbonate, 10–18 parts by weight of refined sugar and 0.1–3.0 parts by weight of silver thiosulfate in water. The said composition is now used for the post-treatment of fiber products and the fermentation of feedstuff and in the agricultural industry by virtue of its high far infrared radiation efficiency, antibacterial activity and deodorizing activity. The composition, however, is disadvantageous in that its preparation is complicated and it is difficult to store for a long period of time.

Meanwhile, the amount of antibiotics used each year in the world is increasing. However, the more antibiotics are used, the greater the side effects are. For example, higher dosages of antibiotics are needed to treat patients who have overused prescription antibiotics because they have become resistant to antibiotics. Furthermore, misuse and abuse of antibiotics has resulted in the appearance of super-bacteria which are completely immune to existing antibiotics. In an effort to curtail the use of antibiotics, consideration has been taken of the general enhancement of the immune system in the body, which leads to an improvement in vaccination effects. For example, nonspecific immunostimulators (hereinafter, referred to as "NIS"), which induce the body to increase its immune response to external pathogens, are now of great interest to medical personnel and extensive and intensive research has been focused on the development of NIS over the world.

In Japan, an ingredient extracted from edible mushroom (*Lentinus edoddes*) was reported to show an anti-cancer effect. In addition, NIS was observed in bacteria one hundred years ago. Along with the effects of forming antibodies and inducing cytokines, the immune enhancement of NIS has recently been under active study. For instance, a cell wall extract from Norcardia opaca is reported to induce the activation of the macrophages derived from murine peritoneal cavities (Barot-Ciobaru et al., 1987). RU41740, derived from Klebsiella pneumoniae, KP-40, derived from Propionibacterium avidum, and QH-B, derived from Quillaja saponaria, are found to have useful functions in association with the induction of cytokines and the stimulation of immune cells (Bessler et al, 1997); Nimier et al., 1999; Ronnberg et al., 1997; Siwiki et al., 19988; Tewari et al., 1996). Recently, bacterial DNA-derived CPG motifs, called immunostimulatory motifs, have been revealed to effectively induce the expression of IL-6, IL-12, IL-18 and IFN-γ in immune cells (Bohle et al., 1999; Klinman et al., 1999; Krieg, 1999).

These and other NIS developed thus far suffer from the problems of being produced in complicated processes, inconvenient for long-term storage, and expensive.

DISCLOSURE OF THE INVENTION

With problems encountered in prior arts in mind, the present invention has an objective of providing an alkaline solution composition, which is easy to produce and store for a long period of time, has inhibitory activity against bacteria and virus proliferation, and can serve as a nonspecific immunostimulator.

It is another object of the present invention to provide a method for preparing such an alkaline solution composition.

It is a further object of the present invention to provide uses of the alkaline solution composition.

It is still a further object of the present invention to provide methods for improving the weight gain rate of livestock and the yield of crops.

It is still another object of the present invention to provide a method for keeping agricultural products, fishes or meats fresh for a long period of time.

It is still yet another object of the present invention to provide a nontoxic, nonspecific immunostimulator with an anticancer effect.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
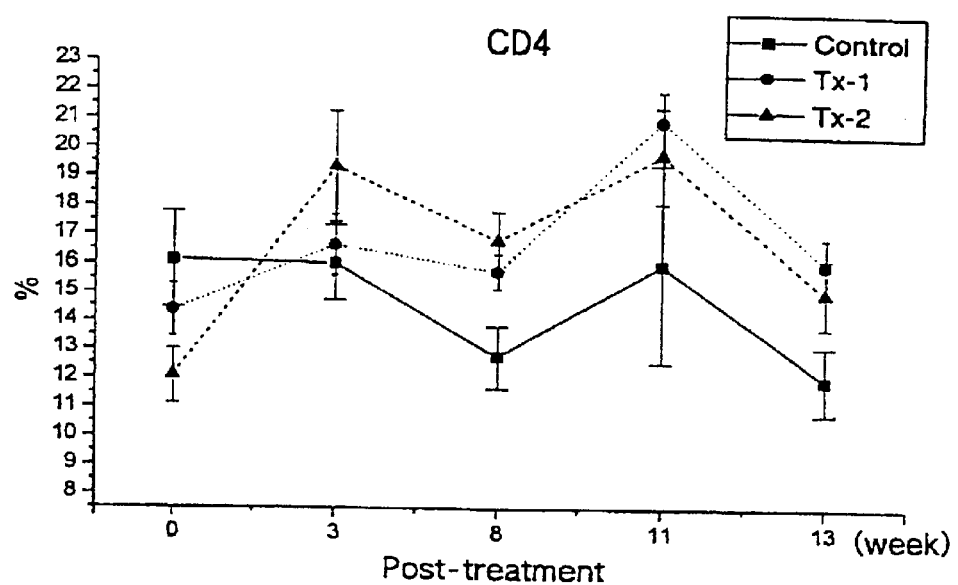
FIG. 1 is a graph in which changes in the proportions of porcine $CD4^+$ T lymphocytes in the BARODON®-fed groups and in the control group are plotted against time.

The present invention contemplates an NIS based on an alkaline solution composition. This composition comprises sodium metasilicate, borax, sodium thiosulfate, potassium carbonate, refined sugar, and water, optionally sodium chloride, silver thiosulfate and/or sodium molybdate.

Sodium metasilicate, useful in the present invention, has five crystalline water molecules and comprises silicon dioxide ($SiO_2$) at an amount of 27.5–29.0% and sodium oxide ($Na_2O$) at an amount of 28.5–30.0% with a content error margin less than 2%. This compound is quite stable compared with commercially available liquid sodium silicate. Existing as a white powder or grain, sodium metasilicate is easy to weigh accurately and convenient for long-term storage and transportation. When being dissolved in water, sodium metasilicate is of strong alkalinity. Silicon, like the other constituents of sodium metasilicate, is an essential element for the growth of animals and plants.

Borax having with ten crystal water molecules has a specific density of 1.715. As a constituent of borax, boron (B) is a trace element in which animals and plants are likely to be deficient. Fruit trees, when soils are insufficient in boron, do not bear well and, if produced, many of their fruits are defective. Generally, borax is used as a bacterium repellent, an insect repellent, a styptic, and a glaze material. When melted together with metals, borax has the property of dissolving the metals. A solution of borax dissolved in water is alkaline with approximately pH 9.5. In the composition of the present invention, the amount of borax is preferably adjusted within the range of 1–15 parts by weight based on 100 parts by weight of sodium metasilicate. For instance, if borax is used at an amount less than 1 part by weight, no effects thereof are exhibited. On the other hand, if the borax content exceeds 15 parts by weight, toxicity may be generated.

With five crystal water molecules, sodium thiosulfate is not dissolved in alcohol, but dissolved in water, giving a characteristic salty taste. Its aqueous solution is neutral with a pH in the range of 6.5–8.0. With a chemical property of dissolving silver halide or other silver salts, sodium thiosulfate is generally used to extract silver from ores. Additionally, sodium thiosulfate finds applications in the removal of chlorine and heavy metals. In the present invention, sodium thiosulfate is used at an amount of approximately $10^{-5}$–$10^{-4}$ parts by weight based on 100 parts by weight of sodium metasilicate. For instance, no additional effects can be obtained when the amount of sodium thiosulfate is less than the lower limit. On the other hand, an amount exceeding the upper limit of sodium thiosulfate, when being applied to animals, acts to sediment tissular Ca, causing the animals to be excited and to have loose bowels.

Potassium carbonate is dissolved well in water and its solution is of strong alkalinity with pH 11.6. Like sodium, potassium is an essential element for the body, playing an important role in metabolism and blood circulation. For example, an appropriate balance between potassium and sodium in vivo is needed to prevent hypertension and diabetes mellitus. In the present invention, a preferable amount of potassium carbonate falls within the range of 30–150 parts by weight based on 100 parts by weight of sodium metasilicate. When being applied to animals or plants, for example, an amount outside this range of potassium carbonate may upset the in vivo balance of sodium/potassium.

In the composition of the present invention, refined sugar prevents ionized inorganic materials from recombining so as to stabilize the composition. In addition, refined sugar converts inorganic materials to organo-type materials in sugar-associated forms, as well as acting to improve the adhesiveness or adsorption of the composition. Within the amount range of 30–200 parts by weight based on 100 parts by weight of sodium metasilicate, refined sugar can perform these roles.

Sodium chloride, an optional compound in the composition of the present invention, is used as a source of sodium to control the ratio of sodium/potassium. As for silver thiosulfate, it is often used to suppress the ethylene synthesis of plants or to facilitate the differentiation of plants. In an aqueous solution, silver thiosulfate forms $[Ag(S_2O_3^{2-})_2]^{3-}$ at a low concentration of $S_2O_3^{2-}$ while forming $[Ag_2(S_2O_3^{2-})_6]^{10-}$ at a high concentration of $S_2O_3^{2-}$. In the present invention, silver thiosulfate, existing in a polyvalent anionic form like sodium thiosulfate, acts to facilitate cell differentiation. In the present invention, sodium molybdate serves as a source of molybdenum, which is an element which animals and plants are likely to lack. The optional compounds are each used at an amount of $10^{-1}$ parts by weight or less based on 100 parts by weight of sodium metasilicate.

After complete dissolution of the constituents, the composition of the present invention is tinged with ivory. The composition is odorless and nontoxic in addition to being very stable with a specific viscosity of 1.43–1.50, maintaining pH 13 and ranging in viscosity from 61.0–239.0. Particularly, even when being treated with HCl, the composition of the present invention hardly undergoes solidification or pH changes.

Various experimental results obtained over a long period of time demonstrate that the composition of the present invention increases weight-gaining rates in livestock and the yield from crops, as well as serving as an excellent NIS in both plants and animals.

The composition of the present invention may be fed to livestock, along with feedstuff, for example, in a mixture with feedstuff or after being fermented in feedstuff, or as a dilution with water. After feeding, the composition brings about excellent immune enhancement in the livestock. For example, the composition of the present invention is effectively preventive of porcine epidemic diarrhea (PED) and hog cholera, which cause serious problems for the hog raising industry. Also, the composition was found to be effective for the prophylaxis and treatment of fowl typhoid, which shows a high mortality, causing an enormous loss in the poultry industry. In the case of milk cows fed with the composition, the somatic cell count per volume of milk, which is an index determining milk quality, was decreased. Other effects of the composition of the present invention on livestock include growth facilitation and improvement in flesh quality. Sheds in which the livestock lived while being fed with the composition of the present invention were found to have less offensive odors than those in which the livestock lived while being fed with ordinary feedstuff.

For plants, the composition of the present invention, which is applied in mixtures of fertilizers or as dilutions in water, exhibits useful effects, including facilitation of germination and growth, improvement in disease resistance, increased crop yields, improvement in crop quality, etc.

A better understanding of the present invention may be obtained in light of the following examples which are set forth to illustrate, but are not to be construed to limit the present invention.

PREPARATION EXAMPLE 1

In purified water (500 kg) maintained at 60–80° C., sodium metasilicate (pentahydrate, 300 kg), borax (decarbohydrate, 35 kg), sodium thiosulfate (0.01 kg), sodium chloride (1 kg), and potassium carbonate (150 kg) were sequentially added, and stirred for 3 hours for dissolution. To the homogeneous solution was added refined sugar (450 kg), followed by stirring for 4 hours to give an alkaline solution with pH 13 (hereinafter referred to as "BARODON®-1").

PREPARATION EXAMPLE 2

BARODON®-1 (1,436 kg), prepared in Preparation Example 1, was dropwise added with a solution of silver thiosulfate (0.02 kg) in water (1 L), stirred and maintained at about 50° C. for 4 hours in an incubator. The resulting solution was designated "BARODON®-2".

PREPARATION EXAMPLE 3

In purified water (5 L) maintained at 100° C., sodium molybdate ($Na_2MoO_4 \cdot 2H_2O$, 0.3 kg) was added with stirring to give a colorless, odorless solution, which was then dropwise added to BARODON®-1, stirred, and maintained at 50° C. for 4 hours in an incubator. The resulting solution was designated "BARODON®-3".

PREPARATION EXAMPLE 4

Using 6 kg of borax and 300 kg of potassium carbonate, an alkaline solution was obtained in a manner similar to that of Preparation Example 1. To the alkaline solution (1,557 kg), a solution of silver thiosulfate (0.02 kg) in water (1 L) was dropwise added, followed by stirring and standing at 50° C. for 4 hours in an incubator. The resulting alkaline solution was designated "BARODON®-4".

PREPARATION EXAMPLE 5

Using 150 kg of refined sugar, the procedure of Preparation Example 4 was repeated to give an alkaline solution with a relatively low viscosity (hereinafter referred to as "BARODON®-5").

EXAMPLE 1

Effect on Rice Cultivation

BARODON®-1 to -5 were tested for immune enhancement and growth facilitation effects on the cultivation of rice plants on paddy fields.

BARODON®-1 to -5 were each diluted in 10 volumes of water and 500-fold diluted again with water. Just after being immersed for 24 hours in the diluted solution, rice seeds were sown on seedbeds. A couple of days before the transplantation of rice plants from the seedbeds to paddy fields, the diluted solutions were sprayed over the nursery rice plants in an ordinary manner. The spraying of the diluted solution was conducted again a couple of weeks before rice booting (rice earing).

On seedbeds, the nursery rice plants treated with the composition of the present invention grew more uniformly and strongly and suffered almost no damages due to cold weather, compared with a control group which was not treated with the composition. Also, the nursery rice plants treated with the composition were observed to completely root only three days after the transplantation. No diseases, including damping-off, leaf blast, and sheath blight, effected the treated rice plants during their growth on field. In addition, the treated rice plants were improved in lodging-resistance and were found to suffer no lodging following a typhoon, while 25% of the control was lodged.

Amounts of produced rice were measured and the results are given in Table 1, below.

TABLE 1

| Composition | Crop yield per $km^2$ (Chuchung ® Rice) |
| --- | --- |
| Control | 575 kg |
| BARODON ®-1 | 655 kg |
| BARODON ®-2 | 690 kg |
| BARODON ®-3 | 710 kg |
| BARODON ®-4 | 680 kg |
| BARODON ®-5 | 670 kg |

EXAMPLE 2

Effect on Pear Tree Cultivation

BARODON®-3 was mixed with 9 volumes of water and then re-diluted 500 times. After applying dung-manure and organic fertilizers on a pear orchard, the dilution was sprayed thereon. Thereafter, a roundabout was installed along the circumference of the orchard to prevent the interference of animals. About a couple of weeks before the blooming of pear blossoms, BARODON®-2 was sprayed on the land. The pear trees fertilized with the compositions of the present invention burst into bloom about 4–5 days earlier and produced harvestable fruits about 15 days earlier than did a control, which was not fertilized with the compositions. The pears harvested from the treated trees were graded the highest in appearance, size and Brix degree. The pears harvested from the trees fertilized with the compositions were 60% reduced in black spot occurrence and smoother in appearance, compared with the control. No soggy pears were found in the treated trees. The pear trees treated with the compositions of the present invention showed a fruit drop rate due to typhoon 20% less than that of the control. The pears of the treated trees were about 15% greater in size compared with those of the control. The Brix degree of the pears of the treated trees was measured to range from 13.0 to 15.0, which was about 12% greater than that of the control. The storage period was also improved.

EXAMPLE 3

Effect on Plant Growth

A 16-fold dilution of BARODON®-3 in water was further diluted by the dilution factors given in Table 2, below and then sprayed over leaves of specimen plants. The leaves were found to be greater by 15.6% in length, 8.7% in width, and 7–47% in foliage fresh weight, compared with a control group which was not treated with the solution.

TABLE 2

| | Pot No. | Leave Width at Maximum (cm) | | | |
|---|---|---|---|---|---|
| | | Dilution Factor | | | Non-Spraying |
| | | 200-Fold | 300-Fold | 400-Fold | |
| 9th day after Spraying (10, July) | 1 | 6.1 | 6.1 | 6.2 | 5.4 |
| | 2 | 6.0 | 6.3 | 6.2 | 5.9 |
| | Avg. | 6.1 | 6.2 | 6.2 | 5.7 |

| | Pot No. | Foliage Fresh Weight (g/pot) | | | |
|---|---|---|---|---|---|
| | | Dilution Factor | | | Non-Spraying |
| | | 200-Fold | 300-Fold | 400-Fold | |
| 9th Day After 2nd Spraying (10, July) | 1 | 57.8 | 59.2 | 44.6 | 39.9 |
| | 2 | 56.3 | 60.5 | 42.8 | 41.5 |
| | Avg. | 57.1 (140%) | 59.9 (147%) | 43.7 (107%) | 40.7 (100%) |

PREPARATION EXAMPLE 6

BARODON®-2, prepared in Preparation Example 2, was diluted by a factor of 10 and 500 g of the resulting dilution was sprayed over 1 ton of combined feedstuff to give a high-functional feedstuff (hereinafter referred to as "BARODON®-6").

PREPARATION EXAMPLE 7

A 10-fold dilution of BARODON®-2, prepared in Preparation Example 2, in water (10 L) was added, together with refined sugar (3 Kg), sodium chloride (1 Kg) and water (75 L), to combined feedstuff (1 ton), after which the resulting formulation was fermented for 24 hours with stirring to give high-functional feedstuff (hereinafter referred to as "BARODON®-7").

EXAMPLE 4

The BARODON® series was tested for weight gain and immune enhancement effects on animals as follows.
(1) Weight-Gaining Effect on Hog 30 heads of three-way cross hybrid (Yorkshire× Landrace×Durroc), fattening hogs, each of which was 15 weeks (104±4 days) old, were selected. They were all admitted to 3 hog pens, each with a size of 4 M×4.2 M, at a population of 10 heads per hog pen and adapted to the new circumstance for one week before testing.

BARODON®-6, prepared in Preparation Example 6, was fed to a group of 10 hogs (designated "Tx-1 group") in one hog pen for 9 weeks while the feedstuff containing 3% of BARODON®-7, prepared in Preparation Example 7, was given to a group of 10 hogs (designated "Tx-2 group") in another hog pen. For a control group, the same feedstuff, but lacking "BARODON®" was supplied. Thereafter, all the hogs were fed with common feedstuff. During the testing period, the hogs were all allowed free access to feedstuff.

A measurement was made of weight gain and feedstuff intake for 6 weeks for each group and, from the measured values, the feed efficiency (feedstuff intake/weight gain) was calculated. The average daily weight gain was measured to be 842.86 g for the control group, 890.48 g for the Tx-1 group and 880.95 g for the Tx-2 group, the latter two groups being 5.65% and 4.52% improved, respectively, compared with the control group. As for average daily feedstuff intake, 2.71 kg of feedstuff was consumed by the control group, 2.77 kg of feedstuff by the Tx-1 group and 2.65 kg of feedstuff by the Tx-2 group. Therefore, the control group showed a feed conversion rate of 3.22 while the Tx-1 group was calculated to be 3.11 in feed conversion rate with an improvement of 3.54% and the Tx-2 group grew at a feed conversion rate of 3.01, which was 6.98% improved.

(2) Perception of Pork

The pork of each of the test groups was tasted by healthy men and women and they were interviewed regarding taste and flesh quality.

TABLE 3

| | Softness of Flesh | | Taste | |
|---|---|---|---|---|
| | Soft | Tough | Good | Moderate |
| Control | 0 | 8 | 0 | 3 |
| Tx-1 | 6 | 1 | 8 | 2 |
| Tx-2 | 11 | 0 | 10 | 0 |

* numbers of the persons who responded to the questions after a sampling party.

(3) Distribution of Immune Cells in Peripheral Blood of Hog

Using pig leukocyte surface-specific monoclonal antibodies and a flow cytometry such as that manufactured by Dickinson Immunocytometry System, San Jose, Calif., U.S.A., identified as FACSCalibur, proportions of major histocompatibility complex (MHC) expressing cells and lymphocyte subpopulations were examined in the peripheral bloods of the Tx-1 and the Tx-2 group as well as the control group.

(3-1) Isolation of Leukocyte from Peripheral Blood

The blood taken from the swine fore vena cava was well mixed with acid citrate dextrose (ACD)-ethylenediamine tetraacetic acid (EDTA) and laid over a layer of Hypaque Ficoll (Histopaque, Sigma, St. Louis, Mo., U.S.A.). After centrifugation at 1,500 rpm for 30 min, leukocytes were taken, washed three times with phosphate buffered saline (PBS, pH 7.2), and suspended in an RPMI-1640 medium (GibcoBRL, Grand Island, N.Y., U.S.A.). For examination, leukocyte cell counts were adjusted to $1 \times 10^7$ cells/ml while viable cells were counted according to the tryphan blue exclusion technique.

(3-2) Monoclonal Antibodies for Examination of Leukocyte Subpopulation

Effects on porcine immunological properties, including immune cell populations, were determined using monoclonal antibodies specifically reactive with cell surface molecules of porcine leukocytes, i.e., MHC class I antigens, MHC class II antigens, Po(porcine)CD2, PoCD4, PoCD8, surface IgM (sIgM), Non T/Non B (γδ TCR), and granulocyte and monocyte (G+M), as shown in Table 4, below.

TABLE 4

| MAb* | Isotype of MAb | Molecules** | Cell type*** | Reference |
|---|---|---|---|---|
| PT85A | IgG$_{2a}$ | MHC class I | All nucleated cells | Davis et al. (1987) |
| H42A | IgG$_{2a}$ | MHC class II | Ag-presenting cells | Davis et al. (1987) |
| TH81A5 | IgG$_{2a}$ | MHC class II | Ag-presenting cells | Davis et al. (1987) |
| MSA4 | IgG$_{2a}$ | PoCD2 | T cells | Davis et al. (1987) |

TABLE 4-continued

| MAb* | Isotype of MAb | Molecules** | Cell type*** | Reference |
|---|---|---|---|---|
| PT90A | IgG$_{2a}$ | PoCD4 | T h/i cells | Davis et al. (1987) |
| PT81B | IgG$_{2a}$ | PoCD8 | T c/s cells | Davis et al. (1987) |
| PIg45A | IgG$_{2b}$ | sIgM | B cells | Davis et al. (1987) |
| PT79A | IgG$_{2a}$ | γδTCR | N cells | Davis et al. (1987) |
| DH59B | IgG$_1$ | Granulocyte + Monocyte | Granulocyte + Monocyte | Davis et al. (1987) |

*MAb: Monoclonal antibodies specifically reactive with leukocyte differentiation.
**Molecules: Porcine leukocyte differentiation molecules.
***Cell type: Cells expressing molecules.

(3-3) Flow Cytometry

Using a flow cytometry CellQuest program, proportions of leukocyte subpopulations were analyzed according to the method of Davis et al (1990). In order to take advantage of a flow cytometry using a laser beam, cells were labeled with one or two fluorescent dyes such as fluorescein isothiocyanate (FITC) and phycoerythrin (PE) in an indirect manner. In each well of a V-bottom 96-well microplate, 100 μl of the leukocytes isolated from blood (cell density 1×10$^7$ cells/ml) was added, along with 50 μl of a monoclonal antibody (concentration 15 μg/ml) and sensitized for 30 min at 4° C., followed by washing three times with a first washing buffer [PBS 450 ml, ACD 50 ml, 20% NaN$_3$ 5 ml, gamma globulin free horse serum (GibcoBRL) 10 ml, 250 mM EDTA 20 ml, 0.5% phenol red 1 ml] through centrifugation. After decanting the supernatant, the cell pellet on the bottom was suspended using a plate mixer or a vortex mixer (Scientific Industries, Bohemia, N.Y., U.S.A.).

In a single dyeing test, an FITC-conjugated goat anti-mouse IgG+IgM antibody (Caltag Lab, U.S.A.), serving as a secondary antibody, was diluted by a factor of 200 and added at an amount of 100 μl to each well in which the suspended leukocytes were contained. After sensitization for 30 min at 4° C., washing was conducted three times with a second washing buffer, which was the same as the first washing buffer, but being free of the horse serum, by centrifugation. A 2% PBS-formalin (38% formalin 20 ml, PBS 980 ml) solution was added at an amount of 200 μl to each well to fix the cells.

In a double dyeing test, PoCD4 (FITC) was coupled with PoCD8 (PE), PoCD4 (FITC) with MHC class II (PE), and PoCD8(FITC) with MHC class II (PE) to dye cells. In detail, leukocyte cells in one well were mixed with a pair of monoclonal antibodies and primarily sensitized according to the result of the single dyeing test, followed by washing three times with the first washing buffer at 4° C. Thereafter, a goat antibody specific for each monoclonal antibody isotype was used at a concentration of 1.0 μg per well for FITC conjugates and at a concentration of 0.1 μg per well for the PE conjugate, followed by secondary sensitization for 30 min at 4° C. Washing and fixing procedures were conducted in the same manner as in the single dyeing test.

After completion of the dyeing, cells were stored at 4° C. in a dark, cold space until examination. Using a flow cytometry, 2,000 or more dyed cells were analyzed to count positive-response cells. In regard to the measurement and data analysis, FACScalibur and CellQuest program (Becton Dickinson) was employed.

The results showed that the proportion of CD4$^+$ T lymphocytes in porcine peripheral blood started to increase after three weeks from the feeding with BARODON®-containing feedstuff, as shown in FIG. 1 and, on the 8$^{th}$ week after the feeding, considerably higher levels of the CD4$^+$ T lymphocytes were maintained by the Tx-1 and the Tx-2 groups than by the control group (p<0.05). Particularly, the Tx-1 group maintained CD4$^+$ T lymphocytes at high levels over a period from the 8$^{th}$ week to the 13$^{th}$ week post-application (p<0.05).

Figure 4:
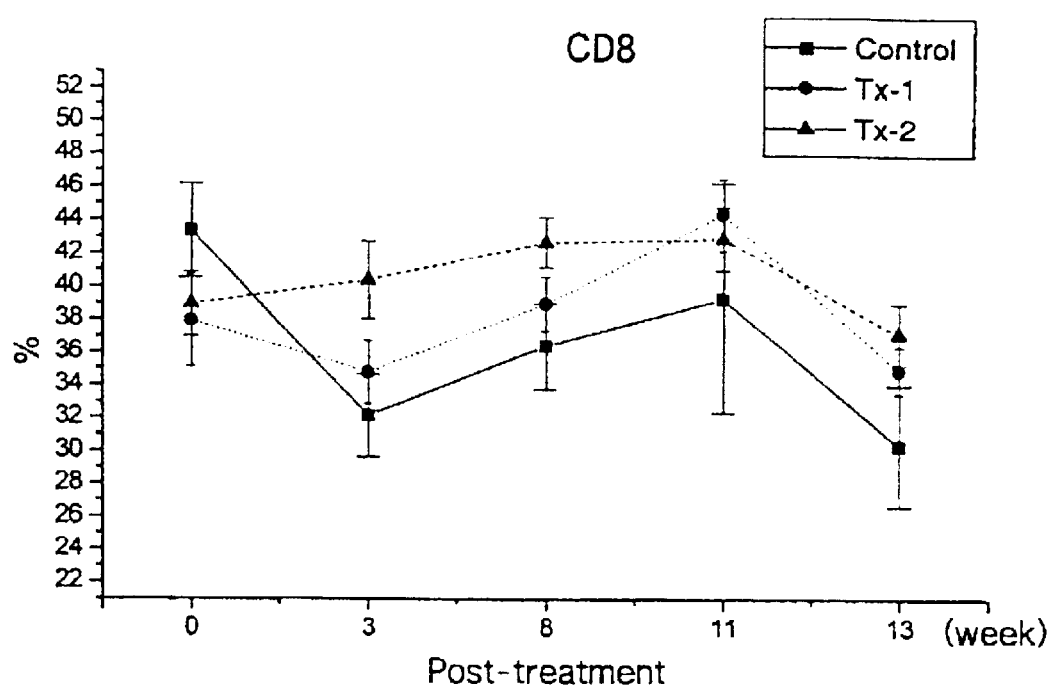
FIG. 4 is a graph in which changes in the proportions of porcine $CD8^+$ T lymphocytes in the BARODON®-fed groups and in the control group are plotted against time.

As for CD8$^+$ T lymphocytes, a high level was detected in the Tx-2 group on the third week after the feeding (p<0.01), but no noticeable differences were found from the 8$^{th}$ week after the feeding, compared with the control group (p<0.05), as shown in FIG. 4.

Figure 2:
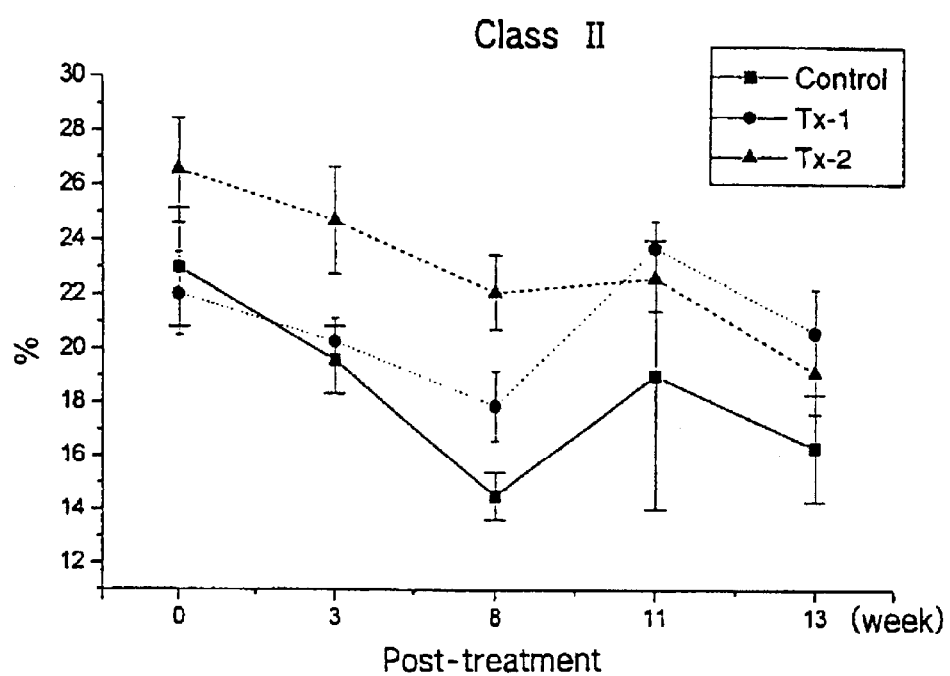
FIG. 2 is a graph in which changes in the proportions of porcine MHC class II-presenting cells in the BARODON®-fed groups and in the control group are plotted against time.

Cells expressing MHC class II antigens, mainly macrophages, were counted at a considerable high level for the Tx-1 group at the 11$^{th}$ week after the feeding (p<0.05) and for the Tx-2 group at the 8$^{th}$ week after the feeding, compared with the control group, as shown in FIG. 2.

Figure 3:
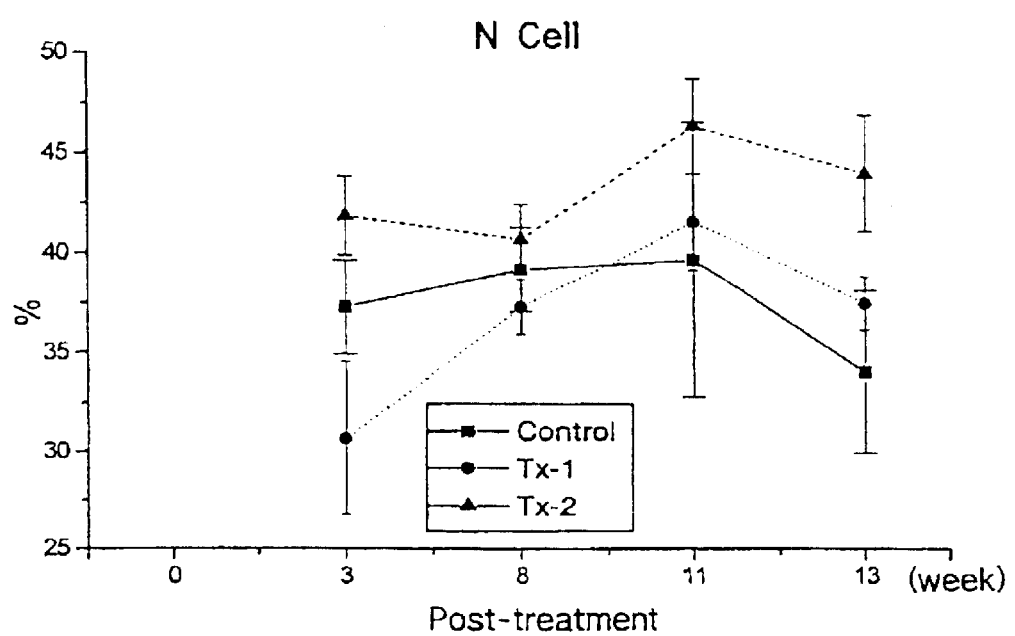
FIG. 3 is a graph in which changes in the proportions of porcine Non T/Non B lymphocytes (N lymphocytes) are plotted against time.

The count of Non T/Non B lymphocytes (N lymphocytes) in the Tx-2 group was maintained higher than that in the control group (p<0.01) from the 3$^{rd}$ week after the feeding, as shown in FIG. 3, showing the possibility of enhancing both nonspecific and specific immune defense responses. Over a period from the 11$^{th}$ week to the 13$^{th}$ week after the feeding, the Non T/Non B lymphocytes were maintained at considerably higher levels in the Tx-2 group than in the control group (p<0.01).

Comparing the two BARODON®-fed groups, the Tx-2 group stayed distinctively predominant over the Tx-1 group in MHC-class II antigen-expressing cell level during a period from the 3$^{rd}$ week to the 8$^{th}$ week after the feeding (p<0.05) as shown in FIG. 2. A little more CD4 and CD8 expressing cells were counted in the Tx-2 group than in the Tx-1 group on the 3$^{rd}$ week after the feeding (p<0.1), as shown in FIGS. 1 and 4. Over the Tx-1 group, the Tx-2 group attained noticeable superiority in Non T/Non B lymphocytes on the 13$^{th}$ week after the feeding, as shown in FIG. 3.

(4) Effect on Activity of Blood and Lymph Nodal Lymphocytes

In order to examine activities of blood and lymph nodal lymphocytes, their proliferative responses were determined by measuring [$^3$H]-thymidine incorporation of porcine lymphocytes obtained from peripheral blood and mesenteric lymph nodes after stimulation with Concanavalin A (Con A), Phytohemagglutinin (PHA), Pokeweed mitogen (PWM) and Lipopolysaccharide (LPS).

Figure 5:
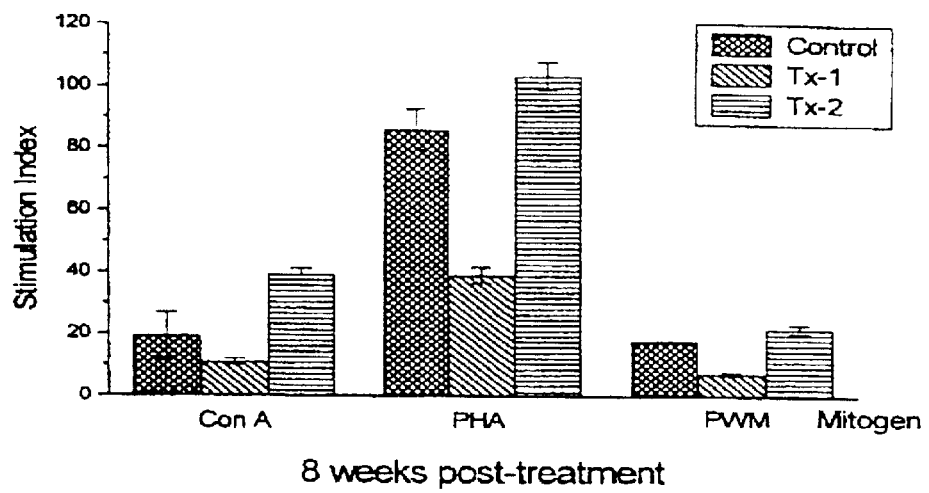
FIG. 5 is a histogram showing the lymphoproliferation activities of porcine lymphocytes isolated from the peripheral blood of the BARODON®-fed groups and the control group in response to stimulation with Con A, PHA, PWM and LPS.
Figure 5:
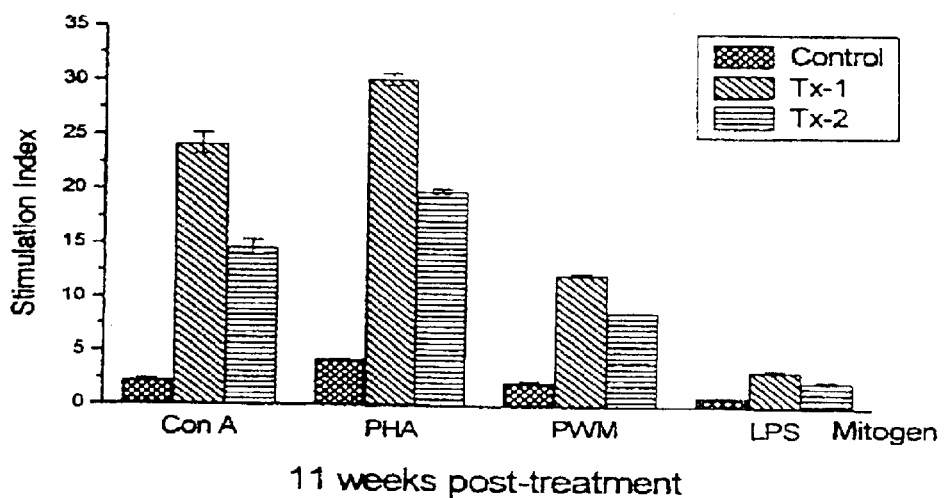

When being stimulated with PWM, the lymphocytes obtained from the peripheral blood of the Tx-2 group after 8 weeks of the feeding with the BARODON®-containing feedstuff were observed to be highly proliferative as proven by a significantly larger stimulation index for the Tx-group than for the control group (p<0.05). At 11$^{th}$ week post-feeding, the lymphocytes isolated from the peripheral blood of both the Tx-1 group and the Tx-2 group gave greater proliferative responses to the stimulation with each of PHA, PWM and LPS than those isolated form the control group, showing higher SI values (p<0.01), as depicted in FIG. 5.

Figure 6:
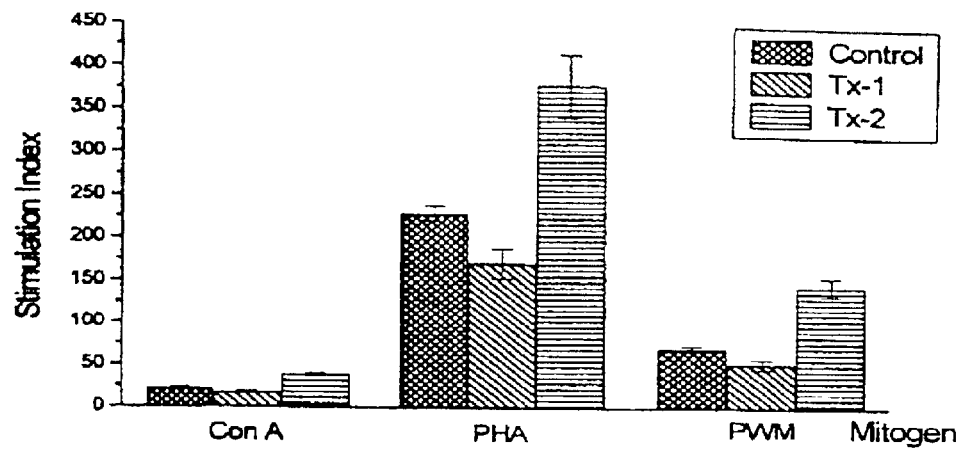
FIG. 6 is a histogram showing the lymphoproliferation activities of porcine lymphocytes isolated from the mesenteric lymph nodes of the BARODON®-fed groups and the control group in response to stimulation with Con A, PHA, PWM and LPS.
Figure 6:
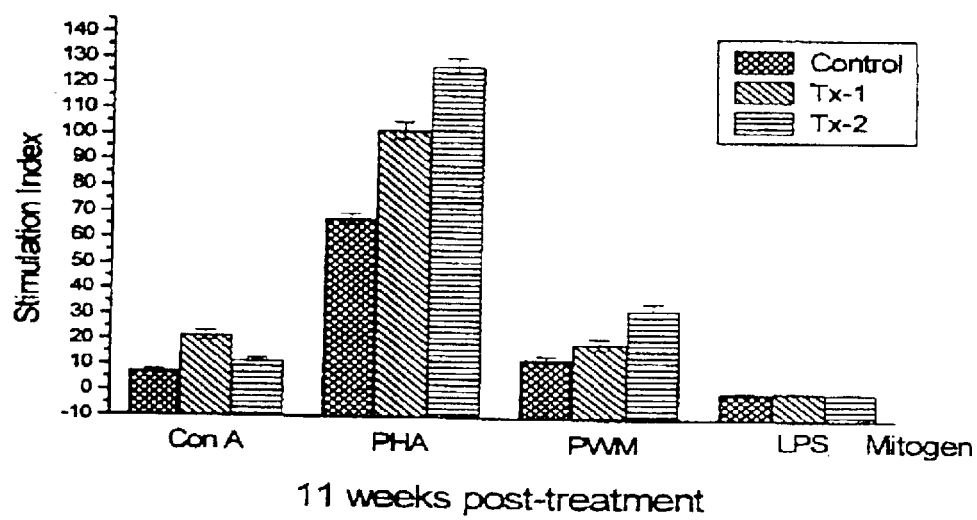

As for lymphocytes isolated from mesenteric lymph nodes, significantly higher SI values were observed in both the Tx-1 group and the Tx-2 group in response to the stimulation with PHA ($p<0.05$) and PWM ($p<0.01$) at the $8^{th}$ week after the feeding than in the control group. At 11 weeks post-application, the Tx-1 group showed higher Con A- and PHA-stimulated lymphoproliferative responses than the control group ($p<0.01$) while the Tx-2 group was measured to have significantly high SI values in response to the stimulation with Con A, PHA and PWM ($p<0.05$), as depicted in FIG. 6.

(5) Effect on Proportions of Splenic and Lymph Nodal $CD4^+$ $CD8^+$ T Lymphocyte Subpopulations Immunohistochemistry was used to analyze proportions of T lymphocytes. After being immunologically dyed by use of the ABC method, $CD4^+$, $CD8^+$, and $CD4^+CD8^+$ dpp T lymphocyte cell counts in mesenteric lymph nodes and spleens were measured with the aid of an image analyzer (Olympus, U.S.A.). The immunohistochemical analysis results are given in Tables 5 and 6, below. In spleens, as apparent from Table 5, an increase was seen in the proportion of $CD4^+$ T lymphocytes for the Tx-2 group only while $CD8^+$ and $CD4^+CD8^+$ T lymphocyte counts were significantly increased for the Tx-1 and the Tx-2 group, both ($p<0.001$). In mesenteric lymph nodes, on the other hand, both the Tx-1 and the Tx2 groups were significantly increased in all $CD4^+$, $CD8^+$ and $CD4^+CD8^+$ dpp T lymphocyte proportions ($p<0.01$), as specified in Table 6, below. Particularly, such higher distributions of T lymphocytes

TABLE 6

| Group | $CD4^+$ | $CD8^+$ | $CD4^+CD8^+$dpp |
|---|---|---|---|
| Control | 32 ± 5 | 29 ± 2 | 10 ± 1 |
| Tx-1 | 35 ± 4 | 39 ± 4 | 32 ± 3 |
| Tx-2 | 40 ± 4 | 47 ± 5 | 35 ± 4 |

(6) Effect on Antibody Production After Vaccination with Hog Cholera Vaccine

Figure 7:
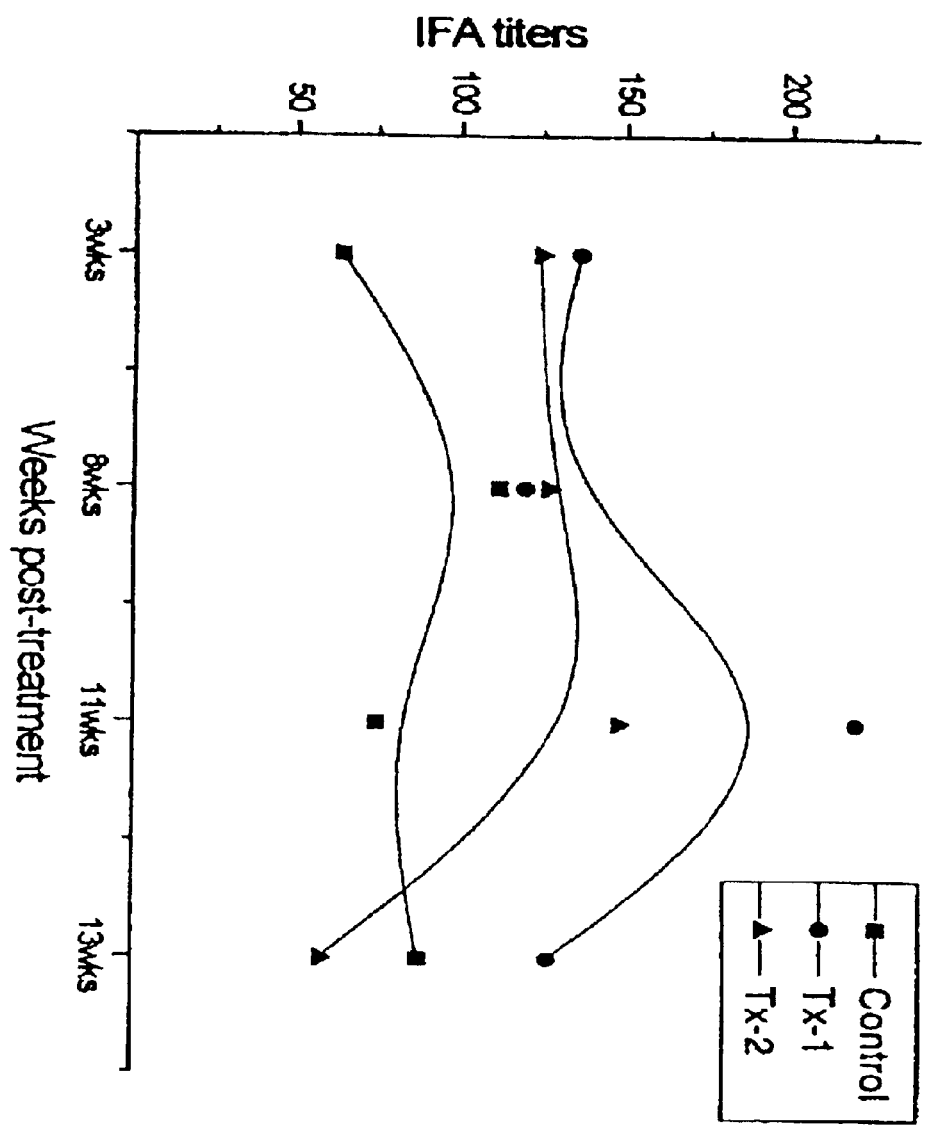
FIG. 7 is a graph showing anti-cholera antibody productivities of the BARODON®-fed groups and the control group.

Anti-hog cholera virus IFA titers were determined after the vaccination with a hog cholera vaccine in BARODON®-fed groups and a non-BARODON® fed group. Significantly higher antibody titers were measured after three weeks of the feeding of BARODON® in the BARODON®-fed groups (Tx-1 and Tx-2) than in the control group and these titers were maintained till the $11^{th}$ week after the feeding ($p<0.01$), as depicted in FIG. 7.

(7) Effect on Typhoid-Resident Fowl Treated with No Antibiotics 10,000 heads of chickens infected with typhoid were fed for 10 weeks with the feedstuff containing 5 wt % of BARODON®-7, prepared in Preparation Example 7. Their mortalities by week were measured and the results are given in Table 7, below. During the testing term, no antibiotics were administered to the typhoid-infected chickens. As specified in Table 7, the BARODON®-fed group showed a mortality of as low as 0.3% on average until the $15^{th}$ week after the testing whereas additional typhoid-infected 10,000 heads in a control group, which were not fed with BARODON®, were, for the most part, dead only 4 days after the testing.

TABLE 7

| Fowl @ | Age (week) | Mortality with Lapse of Time (%) Week | | | | | | | | | | | | | | |
|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| BARODON ®-fed | 27 | .34 | .36 | .31 | .37 | .30 | .28 | .3 | .27 | .3 | .4 | .35 | .33 | .33 | .32 | .31 |
| Control | 28 | 1.12 | 1.45 | 1.73 | 7.19 | almost all dead | | | | | | | | | | | subpopulations were more evident in the Tx-2 group ($p<0.01$).

TABLE 5

| Group | $CD4^+$ | $CD8^+$ | $CD4^+CD8^+$dpp |
|---|---|---|---|
| Control | 11 ± 1 | 8 ± 1 | 3 ± 1 |
| Tx-1 | 11 ± 1 | 11 ± 1 | 6 ± 1 |
| Tx-2 | 14 ± 1 | 17 ± 1 | 11 ± 1 |

(8) Effect on Somatic Cell Count in Milk Cow Suffering from Mastitis

In order to examine the effect of BARODON® on the somatic cell counts of milk cows suffering form mastitis, they were fed with the feedstuff containing 5 weight % of BARODON®-7, prepared in Example 7, for a couple of months. Measurement was made of somatic cell counts. The results are given in Table 8, below, in which the term "liquid medicine" means breasts of the cows were rubbed with towels cleaned with a 100-fold dilution of BARODON®-2, the term "diluted in water" means that the cows were allowed to drink a 200-fold dilution of BARODON®-2, and the character "q" stands for the number of breasts

TABLE 8

| | No. of Somatic Cells (× 1,000) | | | | | | |
|---|---|---|---|---|---|---|---|
| | Farm A | | | | Farm B | | |
| Week After Feeding | Feed + Liquid medicine (q = 10) | Feed (q = 34) | Diluted in Water (q = 6) | Control (q = 37) | Feed + Liquid medicine (q = 16) | Feed (q = 12) | Control (q = 36) |
| Before | 2,457 | 356 | 1,471 | 168 | 967 | 619 | 155 |
| 2 | 1,846 | 205 | 1,999 | 276 | 1,214 | 886 | 197 |
| | (75) | (57) | (135) | (164) | (125) | (150) | (127) |
| 4 | 1,543 | 144 | 1,683 | 371 | 1,017 | 772 | 305 |
| | (62) | (40) | (114) | (220) | (105) | (124) | (196) |
| 6 | 2,001 | 228 | 2,367 | 517 | 1,137 | 681 | 353 |
| | (81) | (64) | (160) | (307) | (117) | (115) | (147) |
| 8 | 1,788 | 272 | 845 | 423 | 936 | 606 | 210 |
| | (72) | (76) | (57) | (251) | (96) | (97) | (135) |

Main pathogens causing mastitis were also counted and the results are given in Table 9, below.

TABLE 9

| | No. of Infected | | | | | |
|---|---|---|---|---|---|---|
| | BARODON ®-fed Group | | | Control | | |
| Pathogen | Pre-Feed | 4 weeks | 8 weeks | Pre-Fee | 4 weeks | 8 weeks |
| Staphylococci sp. | 11 | 7 | 6 | 12 | 14 | 15 |
| Streptococci sp. | 2 | 2 | 1 | 2 | 3 | 3 |
| Gram(−)bacilli | 3 | 2 | 2 | 3 | 4 | 4 |
| Fungi/Bacili | 0 | 0 | 0 | 1 | 2 | 2 |
| Total | 16 | 11 | 9 | 18 | 23 | 24 |

EXAMPLE 5

BARODON® was also investigated for its immune enhancement of the human body. In this regard, texts for children were manufactured with sheets of paper, over which a 100-fold dilution of BARODON®-5, prepared in Preparation Example 5, had been sprayed, and measured for QRS waves in Japanese Far InfraRed Ray Application Institute, located in Osaka, Japan. The results are given in Table 10, below. For reference, QRS wave numbers can give physically beneficial effects to the body when being within the range of 10,000 to 20,000.

TABLE 10

| | Wave No. | |
|---|---|---|
| | BARODON ®-S.F Paper | Non-treated Paper |
| Allergy | 1,700 | 11 |
| Ocular Nerve | 1,300 | 13 |
| Autonomic Nerve | 1,500 | 11 |

EXAMPLE 6

Toxicity Test

The toxicity of BARODON® was determined through in acute toxicity tests using rats at Screening and Toxicology Center of the Korea Research Institute of Chemical Technology (Test No. S-700). The acute tests were conducted with a 10-fold dilution of BARODON®-4, according to the National Institute of Health's Notification No. 94-3 'Toxicity Testing Practice for Medicines' (Apr. 14, 1994) and the Ministry of Health and Welfare's Regulation No. 87-80 'Korean Good Laboratory Practice' (Oct. 29, 1987).

As a result of the test, toxic symptoms, including death, eight change, and other side effects, were not observed in males and females injected with the testing material while the $LD_{50}$ value was reported to be over 5,000 mg/kg for male and female, both. This means that the composition of the present invention is non-toxic to human bodies.

EXAMPLE 7

Mutation Test

To determine whether BARODON® acts as a mutagen, a returning mutation test was carried out at Screening and Toxicology Center of the Korea Research Institute of Chemical Technology (Test No. S-694) in accordance with the National Institute of Health's Notification No. 94-3 'Toxicity Testing Practice for Medicines' (Apr. 14, 1994) and the Ministry of Health and Welfare's Regulation No. 87-80 'Korean Good Laboratory Practice' (Oct. 29, 1987), treating four salmonella strains (His-less mutants of *Salmonella typhimurium* TA100/TA1535 (base pair substitution type) and TA98/TA1537 (frame shift type) with a 10-fold dilution of BARODON®-4.

From all the four bacterial strains, negative records were observed, indicating that the test material did not cause the return mutation from $His^-$ strains into $His^+$ ones. This result means that the composition of the present invention is safe to the human body.

EXAMPLE 8

Effect on Cell Proliferation of Oosperm

Immature ova recovered from cow ovaries were subjected to in vitro maturation for 24 hours and then to in vitro fertilization for 20 hours. The resulting oosperms were developed for 9 days in media in which a 10-fold dilution of BARODON®-4 was further diluted by factors of 500, 200, 100 and 50, respectively and in control media. Bull spermiducts, obtained from a local slaughter house, and bovine oviduct epithelial cells (BOEC) and granulosa cells (GC), both taken from cow ovaries, were cultured to the third generation in the same media. Viable cells were counted using a hemocytometer.

After the development, the externally fertilized oosperms underwent cleavage at a rate of 60.0% in the control media, at a rate of 62.4% in the 500-fold diluted media, at a rate of 66.3% in the 200-fold diluted media, and at a rate of 73.7% in the 50-fold diluted media. Development rates of the blastocyst embryos were measured to be 13.3% in the control media, 20.0% in the 500-fold diluted media, 21.3% in the 200-fold diluted media, 18.4% in the 100-fold diluted media, and 11.0% in the 50-fold diluted solution. After culturing, viable cells numbered $2.0 \times 10^5$ cells for BOEC and $3.2 \times 10^5$ cells for GC in the control media, $2.4 \times 10^5$ cells for BOEC and $3.9 \times 10^5$ cells for GC in the 500-fold diluted media, $2.5 \times 10^5$ cells for BOEC and $3.7 \times 10^5$ cells for GC in the 200-fold diluted media, $2.6 \times 10^5$ cells for BOEC and $2.7 \times 10^5$ cells for GC in the 100-fold diluted media, and $2.5 \times 10^5$ cells for BOEC and $2.8 \times 10^5$ cells for GC in the 50-fold diluted media.

As demonstrated in the above data, the composition of the present invention has a positive influence on both the cell proliferation of BOEC and GC and the proliferation and development of oosperms and blastocyst embryos. Particularly, blastocyst embryos were improved in proliferation rate by 50.4–60.2% when being cultured in the 500-fold and 200-fold diluted media, compared with when being cultured in the control media.

EXAMPLE 9

Anti-Cancer Activity

After being diluted by factors of 600–900, BARODON®-4 was tested for inhibitory activity against human tumor (cancer) cells of four kinds.

Human leukemic cells (Jurkat), human lung carcinoma cells (NCl-H69), human stroma cells (SW579), and human osteogenic sarcoma cells (U-2 OS) were obtained from the American Type Culture Collection, Rockvile, Md., U.S.A. Each of these cells was cultured in media in which BARODON®-4 was diluted by factors of 600, 700, 800 and 900. Cells were examined and measured for their proliferation rates at each sub-culturing while viable cells were counted using a tryphan blue method.

Prior to the examination of anticancer activity, normal cells were cultured in the same diluted media to determine whether BARODON® has cytotoxicity. The results are given in Table 11, below, demonstrating that the diluted media did not inhibit the growth rate of human fibroblast cells nor prevented the proliferation of hamster kidney cells.

TABLE 11

| Cell lines | Culture Media | Dilution of BARODON®-4 | No. of passages | Condition of Cells* |
|---|---|---|---|---|
| CCD-27SK (Normal skin fibroblasts | DMEM + 10% FCS | Control | P8 | Excellent |
|  |  | 1/900 | P8 | Excellent |
|  |  | 1/800 | P8 | Excellent |

TABLE 11-continued

| Cell lines | Culture Media | Dilution of BARODON®-4 | No. of passages | Condition of Cells* |
|---|---|---|---|---|
| of human |  | 1/700 | P8 | Very good |
|  |  | 1/600 | P7 | Poor |
| BHK-21 Normal hamster kidney cells | DMEM + 10% FCS | Control | P17 | Excellent |
|  |  | 1/900 | P17 | Excellent |
|  |  | 1/800 | P17 | Very good |
|  |  | 1/700 | P17 | Good |
|  |  | 1/600 | P11 | Poor |

*dyed with 0.4% tryphan blue and counted under a microscope

Culture results of the cancer cells of four kinds are given in Table 12, below.

TABLE 12

| Cell Lines | Culture Media | Dilution of BARODON®-4 | No. of passages | Condition of cells* |
|---|---|---|---|---|
| Jurkat leukemic leukocytes of human | RPMI-1640 + 10% FCS | Control | P7 | Excellent |
|  |  | 1/900 | P7 | 97% Died in P7 |
|  |  | 1/800 | P7 | 99% Died in P7 |
|  |  | 1/700 | P2 | 99% Died in P2 |
|  |  | 1/600 | P2 | 100% Died in P2 |
| NCI-H69 Small cell carcinoma of human lung | RPMI-1640 + 10% FCS | Control | P6 | Excellent |
|  |  | 1/900 | P6 | 81% Died in P6 |
|  |  | 1/800 | P5 | 98% Died in P5 |
|  |  | 1/700 | P2 | 100% Died in P2 |
|  |  | 1/600 | P2 | 100% Died in P2 |
| SW579 Thyroid carcinoma of human | RPMI-1640 + 10% FCS | Control | P10 | Excellent |
|  |  | 1/900 | P10 | Excellent |
|  |  | 1/800 | P10 | Excellent |
|  |  | 1/700 | P10 | Very good |
|  |  | 1/600 | P9 | Good |
| U-20S Osteogenic Sarcoma of human | Mccoy's 5A + 15% FCS | Control | P10 | Excellent |
|  |  | 1/900 | P10 | Excellent |
|  |  | 1/800 | P10 | Very good |
|  |  | 1/700 | P9 | 39% Died in P2** |
|  |  | 1/600 | P9 | 47% Died in P2** |

*dyed with 0.4% tryphan blue and counted under a microscope
**100% dead after P3

As apparent from Tables 11 and 12, the compositions of the present invention have inhibitory activity against human tumor cells while giving no damages to normal cells. Therefore, the present invention can be used for the effective treatment of human tumors of some kinds even though the efficacy may be different depending on kinds of tumors.

EXAMPLE 10

Effect on Freshness Retention

Fresh cods were flash-frozen with dry ice before being transported to a laboratory. After being immersed in one of a BARODON®-free solution, a 0.05%, 0.1% or 0.5% BARODON®-2 solution for 10 min, they were stored at 0° C. for 7 days during which their freshness was examined.

Figure 8:
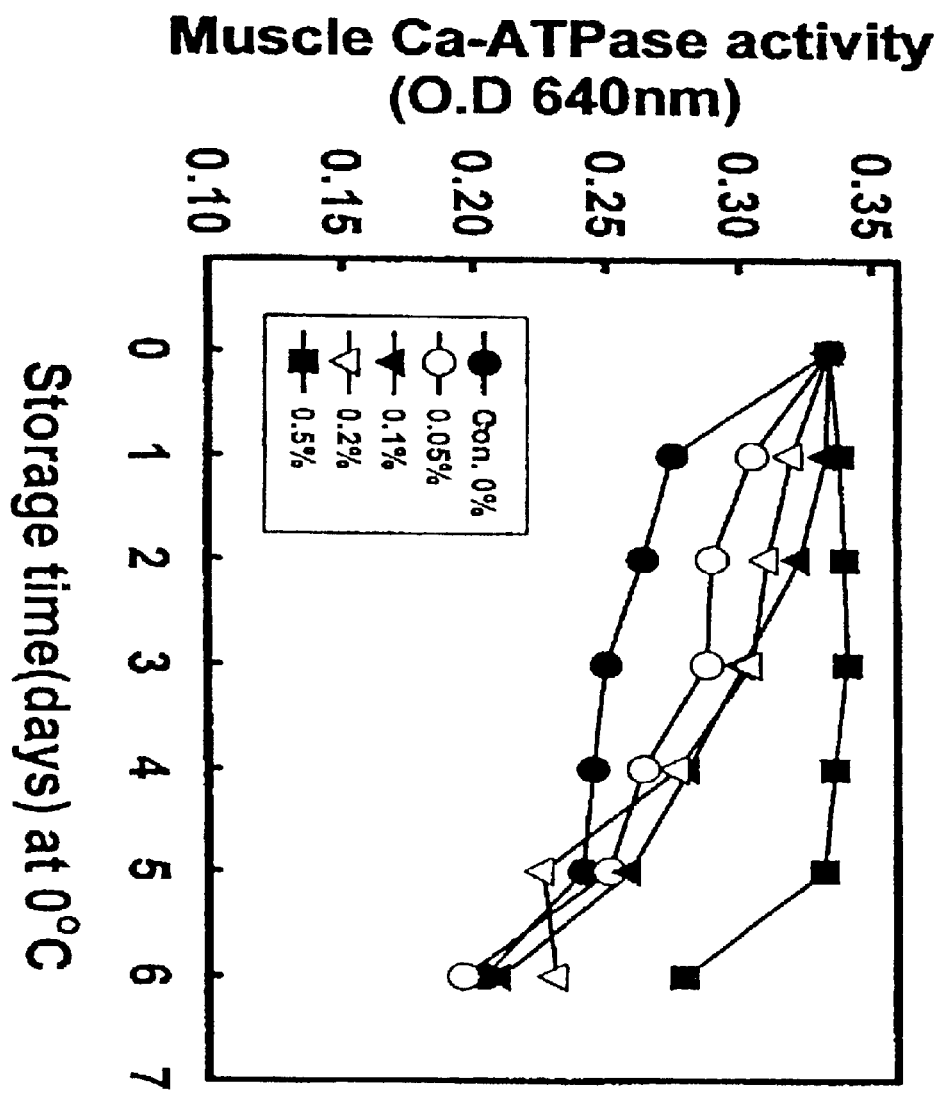
FIG. 8 is a graph in which changes in muscle Ca-ATPase activity of cods in the BARODON®-treated groups and the control group are plotted against storage time.

As a fresh index for fishes, the activity of muscular Ca-ATPase, which is connected with protein denaturation, was measured in the subjects. The best results were observed in the cods immersed in the 0.5% BARODON®-2 solution, indicating the retention of the original freshness for 5 days, as shown in FIG. 8.

EXAMPLE 11

Effect on Water Activation

Figure 9:
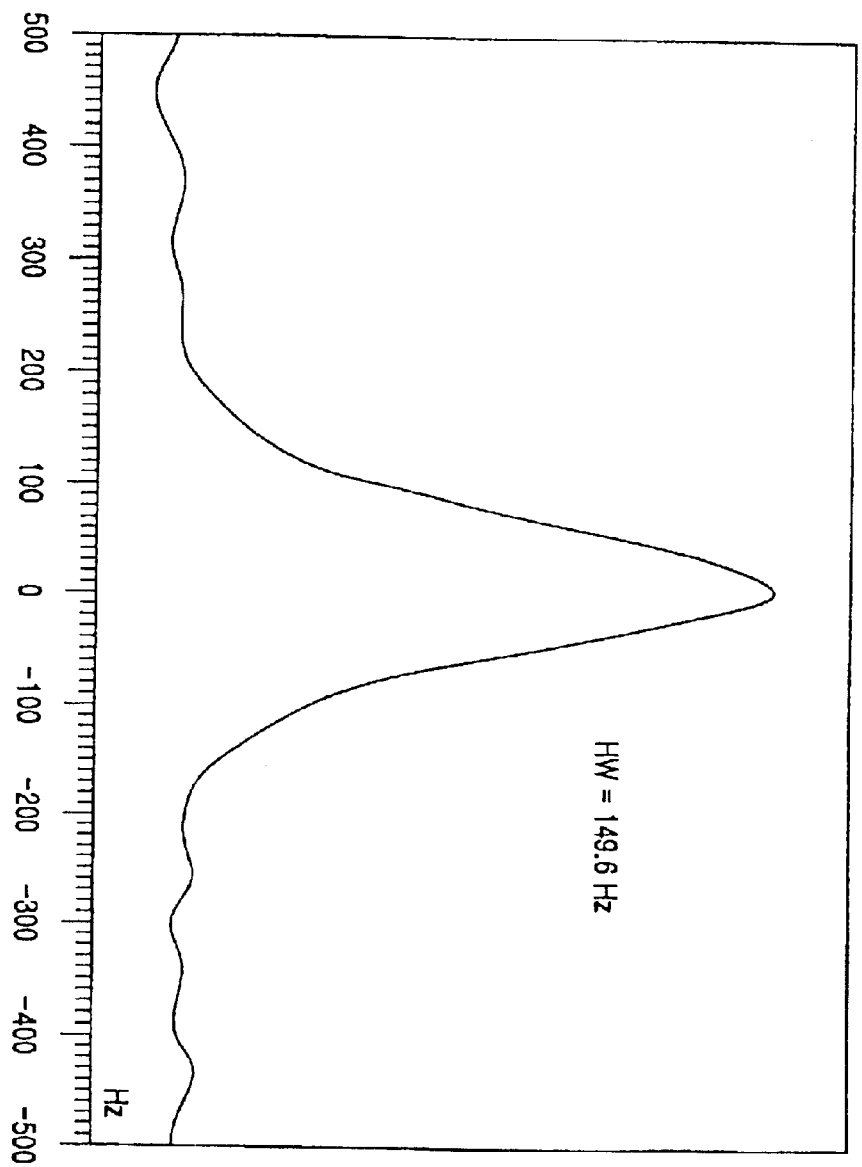
FIG. 9 is an NMR spectrum showing an absorption wavelength band for $^{17}O$ of tap water.
Figure 10:
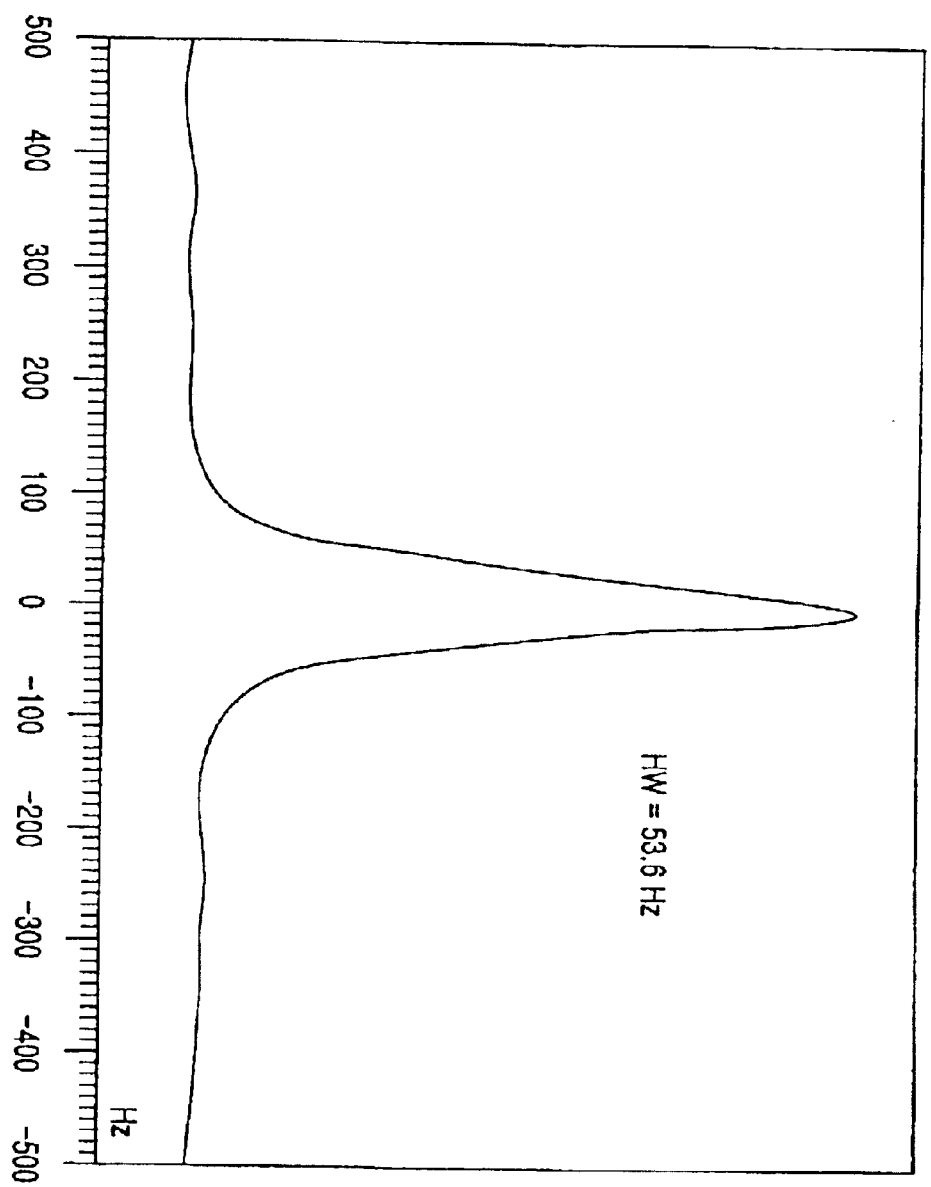
FIGS. 10 and 11 are NMR spectra showing absorption wavelength bands for $^{17}O$ of water molecules in an aqueous solution containing the composition of the present invention.
Figure 11:
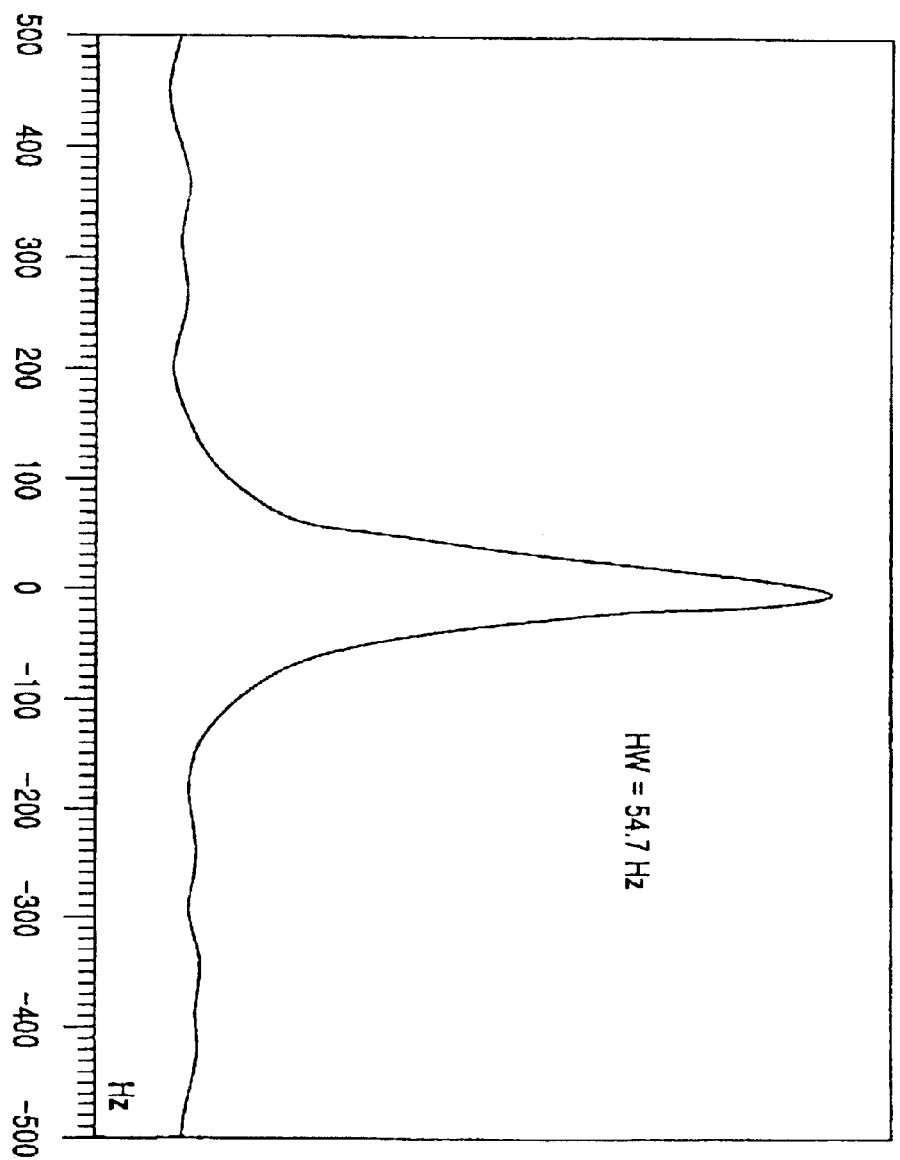

Aqueous solutions in which BARODON®-5 was diluted at dilution ratios of 1:2,800 and 1:5,600 with tap water were measured for $^{17}$O-NMR of $H_2O$. The spectroscopic examination was conducted at 20° C. with the aid of a spectrophotometer JNM-EX270 at the Japanese Water Science Research Meeting, Japan, using as a control tap water. $^{17}$O absorption wavelength bands were measured at 149.6 Hz (full width at half maximum) for the control (FIG. 9), 53.6 Hz for the 2,800-fold diluted solution (FIG. 10), and 54.7 Hz for the 5,600-fold diluted solution (FIG. 11).

These spectroscopic analysis results indicated that the tap water is of a heterologous phase, resulting from the aggregation of various water molecule combinations which differ from one to another in the number of bound water molecules whereas the BARODON®-containing solutions are of near crystalline phases in which water molecule combinations are composed of constant, minimal numbers of bound water molecules. With smaller numbers of bound water molecules, water is in a more active state, showing better fluidity and biopermeability. Because activated water can be useful for the growth of animals and plants, the composition of the present invention can be used as a beverage additive or a wastewater-treating agent.

EXAMPLE 12

Behavior of BARODON® Upon Neutralization

BARODON®-4, prepared in Preparation Example 4, was of strong alkalinity with pH 13.20. When BARODON®-4 was neutralized with 0.1 N HCl, a precipitate formed at the contact area. Further, the composition did not show detectable pH change even after addition of a considerable amount of HCl. This behavior indicates that the composition of the present invention is highly reactive because of being sufficiently ionized.

While a 1,000-fold dilution of the composition was neutralized with 0.1 N HCl, neither coagulates nor bubbles were observed under a microscope. In this case, a change occurred in the pH.

From this behavior of BARODON® upon neutralization, it can be recognized that, when being used at an appropriate amount, the composition of the present invention does not produce coagulates after the reaction with HCl within human and animal stomach. In addition, no gas is produced by the introduction of the present invention in the stomach, so that the composition is free of the problems associated with gas production.

When being applied to animals and plants, as described hereinbefore, the composition of the present invention can bring about an improvement in disease resistance, weight gain rate, crop yield, crop quality, harvest time. Also, the composition of the present invention shows nonspecific immunostimulating activities, including antibody production and immune enhancement, by activating immune cells, thereby maximizing vaccination effects versus malignant virus diseases.

With remarkable inhibitory activity against some kinds of human tumors, the composition of the present invention can be used as a therapeutic or a preventive agent.

In addition, when the composition of the present invention is fed in mixture with feedstock to livestock, the sheds in which the livestock lived were found to have less offensive odors and the feedstuff is little infested with noxious insects. Further, the composition of the present invention is highly useful as a preservative for keeping foods fresh.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A method for promoting the differentiation of human or animal oosperms, in which an effective amount of a composition comprising 100 parts by weight of sodium metasilicate ($Na_2SiO_3 \cong H_2O$), 1–15 parts by weight of borax ($Na_2B_4O_7 \cong 10H_2O$), $10^{-5}$–$10^{-4}$ parts by weight of sodium thiosulfate ($Na_2S_2O_3 \cong 5H_2O$), 30–150 parts by weight of potassium carbonate, 30–200 parts by weight of refined sugar ($C_{12}H_{22}O_{11}$), and 100–200 parts by weight of water or a dilution thereof is administered to humans or animals in need thereof.

* * * * *